(12) United States Patent
Mor et al.

(10) Patent No.: US 7,541,182 B2
(45) Date of Patent: Jun. 2, 2009

(54) IN VITRO TEST TO DETECT RISK OF PREECLAMPSIA

(75) Inventors: Gil G. Mor, Cheshire, CT (US); Donna Neale, New Haven, CT (US); Roberto Romero, Grosse Pointe Farms, MI (US)

(73) Assignees: Yale University, New Haven, CT (US); The United States of America as represented by the Department of Health and Human Services, Washington, DC (US)

( * ) Notice: Subject to any disclaimer, the term of this patent is extended or adjusted under 35 U.S.C. 154(b) by 116 days.

(21) Appl. No.: 10/779,360

(22) Filed: Feb. 13, 2004

(65) Prior Publication Data

US 2005/0074746 A1 Apr. 7, 2005

Related U.S. Application Data

(60) Provisional application No. 60/516,296, filed on Nov. 3, 2003, provisional application No. 60/447,140, filed on Feb. 13, 2003.

(51) Int. Cl.
*C12N 5/08* (2006.01)
(52) U.S. Cl. .................................................... 435/372
(58) Field of Classification Search ........................ None
See application file for complete search history.

(56) References Cited

OTHER PUBLICATIONS

Neala et al. Meeting abstract. Am J Obstetrics and Gynecology 2001;185(6-s1) p. s83.*
Khong, T.Y., et al., "Inadequate maternal vascular response to placentation in pregnancies complicated by preeclampsia and by small-for-gestational age infants," Br J Obstet Gynaecol, 93: 1049-59 (1986).
Zhou, Y. et al., "Preeclampsia is associated with failure of human cytotrophoblasts to mimic a vascular adhesion phenotype. One cause of defective endovascular invasion in this syndrome?", J Clin Invest, 99: 2152-64 (1997).
Fisher, S.J., "The placenta dilemma," Semin Reprod Med, 18: 321-6 (2000).
DeWolf, F., et al., "Ultrastructure of the spiral arteries in the human placental bed at the end of normal pregnancy," Am J Obstet Gynecol, 117: 833-48 (1973).
Buemi, M., et al., "Is apoptosis cause of preeclampsia?", Eur Rev Med Pharmacol Sci, 2: 185-8 (1998).
Levy, R., et al., "To be, or not to be, that is the question. Apoptosis in human trophoblast" Placenta, 21: 1-13 (2000).

Mor, G., et al., "Role of the Fas/Fas ligand system in female reproductive organs: survival and apoptosis," Biochem Pharmacol, 64: 1305 (2002).
Straszewski, S.L., et al., "Confers Human Trophoblast Cell Resistance to Fas-Mediated Apoptosis," Molecular Human Reproduction (2004) in press.
Smith, S.C., et al., "Increased placental apoptosis in intrauterine growth restriction," Am J Obstet Gynecol, 177: 1395-401 (1997).
Levy, R., et al., "Trophoblast apoptosis from pregnancies complicated by fetal growth restriction is associated with enhanced p53 expression," Am J Obstet Gynecol, 186: 1056-61 (2002).
Smith, S.C., et al., "Placental apoptosis in normal human pregnancy," Am J Obstet Gynecol, 177: 57-65 (1997).
Aschkenazi, S., et al., "Differential regulation and function of the fas/fas ligand system in human trophoblast cells," Biol Reprod, 66: 1853-61 (2002).
Chua, S., et al., "Trophoblast deportation in pre-eclamptic pregnancy," Br J Obstet Gynaecol, 98: 973-9 (1991).
Johansen, M., et al., "Trophoblast deportation in human pregnancy—its relevance for preeclampsia," Placenta, 20: 531-9 (1999).
Sargent, I.L., et al., "Clinical experience: isolating trophoblasts from maternal blood," Ann N Y Acad Sci., 731: 154-61 (1994).
Knight, M., et al., "Shedding of syncytiotrophoblast microvilli into the maternal circulation in pre-eclamptic pregnancies," Br J Obstet Gynaecol, 105: 632-40 (1998).
Kertesz, Z., et al., "Purification and characterization of a complex from placental syncytiotrophoblast microvillous membranes which inhibits the proliferation of human umbilical vein endothelial cells," Placenta, 20: 71-9 (1999).
Mor, G., et al., "Fas-Fas ligand system induced apoptosis in human placenta and gestational trophoblastic disease," American Journal of Reproductive Immunology, 40: 89-95 (1998).
Athayde, N., et al., "Interleukin 16 in pregnancy, parturition, rupture of fetal membranes, and microbial invasion of the amniotic cavity," Am J Obstet Gynecol, 182: 135-41 (2000).
Romero, R., et al., "Further observations on the fetal inflammatory response syndrome: a potential homeostatic role for the soluble receptors of tumor necrosis factor alpha," Am J Obstet Gynecol, 183: 1070-7 (2000).
Rudin, C.M., et al., "Apoptosis and disease: regulation and clincal relevance of programmed cell death," Annu Rev Med, 48: 267-81 (1997).

(Continued)

*Primary Examiner*—John P Weber
*Assistant Examiner*—Bin Shen
(74) *Attorney, Agent, or Firm*—Wolf, Greenfield & Sacks, P.C.

(57) ABSTRACT

The present invention provides methods for identifying patients at risk of developing preeclampsia. In further embodiments, the present invention relates to methods for the diagnosis of patients with preeclampsia.

7 Claims, 6 Drawing Sheets

OTHER PUBLICATIONS

DiFederico, E., et al., "Preeclampsia is associated with widespread apoptosis of placental cytotrophoblasts within the uterine wall," Am J Pathol, 155: 293-301 (1999).

DeWolf, F., et al., "The ultrastructure of acute atherosis in hypertensive pregnancy," Am J Obstet Gynecol, 123, 164-74 (1975).

Roberts, JM, "Preeclampsia: What We Know and What We Do Not Know," Semin Perinatol 24: 24-8 (2000).

The Magpie Trial Collaborative Group, "Do women with pre-eclampsia, and their babies, benefit from magnesium sulphate? The Magpie Trial: a randomized placebo-controlled trial," Lancet 359: 1877-90 (2002).

Williams, J.W., "Premature separation of the Normally Implanted Placenta," Surg Gynecol Obstet 21(5): 541-554 (1915).

Chesley, L.C., "The Control of Hypertension in Pregnancy," Obstet Gynecol Annu 10: 69-106 (1981).

Tatum, H.J. and Mule, J.G., The hypertensive action of blood from patients with pre-eclampsia, Am J Obstet Gynecol 83: 1028-35 (1962).

Tatum, H.J., "The Obstetric Patient with Toxemia," Clin Obstet Gynecol 13: 233-48 (1964).

Pirani, B.B. and MacGillivray, I., "The effect of plasma retransfusion on blood pressure in the puerperium,", AM J Obstet Gynecol 121: 221-6 (1975).

Gant, N.F., et al., "The Nature of Pressor Responsiveness to Angiotensin II in Human Pregnancy," Obstet Gynecol 43(6): 854 (1974).

Gant, N.F., et al., "A Study of Angiotensin II Pressor Response throughout Primigravid Pregnancy," J Clin Invest 52: 2682-9 (1973).

Zuspan, F.P., "Catecholamines: Their Role in Pregnancy and the Development of Pregnancy-Induced Hypertension," J Reprod Med 23(3): 143-50 (1979).

Zuspan, F.P., "Urinary amine alterations in drug-addiction pregnancy," Am J Obstet Gynecol 126(7): 955-64 (1976).

Krege, J.H. and Katz, V.L., "A Proposed Relationship Between Vasopressinase Altered Vasopressin and Preeclampsia," Med Hypotheses 31: 283-7 (1990).

McKinney, E.T., et al., "Plasma, urinary, and salivary 8-epi-prostaglandin $f_{2\alpha}$ levels in normotensive and preeclamptic pregnancies," Am J Obstet Gynecol 183(4): 874-7 (2000).

Clark, B.A., et al., "Plasma endothelin levels in preeclampsia: Elevation and correlation with uric acid levels and renal impairment," Am J Obstet Gynecol 166(3): 962-8 (1992).

Pedersen, E.B., et al., "Renin, Angiotensin II, Aldosterone, Catecholamines, Prostaglandins and Vasopressin. The Importance of Pressor and Depressor Factors for Hypertension in Pregnancy," Scand J Clin Lab Invest Suppl 169: 48-56 (1984).

Aalkjaer, C., et al., "Morphology and Angiotensin II Responsiveness of Isolated Resistance Vessels from Patients with Pre-eclampsia," Scand J Clin Lab Invest Suppl 169: 57-60 (1984).

Neale, D., et al., "Maternal serum of women with pre-eclampsia reduces trophablast cell viability: evidence for an increased sensitivity to Fas-mediated apoptosis," J Matern Fetal Neonatal Med 13: 39-44 (2003).

Polliotti, et al. "Second-Trimester Maternal Serum Placental Growth Factor and Vascular Endothelial Growth Factor for Predicting Severe, Early-Onset Preeclampsia", *Obstetrics & Gynecology*, 101: 1266-1274, (2003).

* cited by examiner

FIGURE 3

|  | NORMAL | PRE DISEASE | p value |
|---|---|---|---|
| Number of patients | 58 | 38 | ns |
| Mean age (yrs) | 27.39 | 27.27 | ns |
| Gravida | 2.29 | 1.97 | ns |
| Mean gestational age at blood draw (wks) | 23.14 | 20.38 | ns |
| Nulliparous (N) | 7 | 15 | >.05 |

IN VITRO TEST TO DETECT RISK OF PREECLAMPSIA

RELATED APPLICATIONS

This application claims the benefit of the filing date of U.S. Provisional Application No. 60/447,140, entitled "In vitro test to detect risk of preeclampsia", by Guillermo G. Mor, Donna M. Neale, and Roberto Romero (filed Feb. 13, 2003), and of the filing date of U.S. Provisional Application No. 60/516,296 (filed Nov. 3, 2003). The entire teachings of the referenced Provisional Applications are incorporated herein by reference.

FUNDING

Work described herein was funded, in whole or in part, by National Institutes of Health grants RO1 HD37137-01A2 and RO1 CA92435-01. The United States government has certain rights in the invention.

BACKGROUND OF THE INVENTION

Preeclampsia complicates up to 8% of pregnancies and accounts for significant perinatal morbidity and mortality (1, 2). No definitive etiology or specific predictors of the disease has been identified to date. Furthermore, there has been little progress in the treatment of this disorder, as the cure remains delivery of the fetus and removal of the placenta.

As early as 1915, Williams hypothesized the presence of toxic factors in the blood of women with the clinical syndrome of "toxemia" or preeclampsia (25). A number of subsequent studies, aimed at determining whether blood from pregnant women or placental extracts contained factors responsible for hypertension, yielded contradictory results (26-28). Tatum and Mule reported that whole blood collected from patients with severe preeclampsia could induce transient hypertension when transfused to the same patient in the post partum period (28). Pirani and Macgillivray reported similar observations after injecting plasma from eclamptic women 6 days after delivery (29). Since the increase in blood pressure could not be elicited by re-transfusion 6 weeks postpartum, the authors concluded that patients with preeclampsia had increased sensitivity to pressor agent(s) lasting about 1 week after delivery, but not as long as 6 weeks. Thereafter, considerable effort was devoted to the identification of the pressor agent responsible for this effect in the maternal circulation. Over the years, the focus has encompassed the renin-angiotensin system (30, 31), norepinephrine (32, 33), vasopressin (34), prostaglandins (35), endothelin (36) and others (37, 38). Despite all efforts, the factor(s) responsible for these effects remains to be elucidated.

It would be useful to be able to identify patients at risk of developing preeclampsia.

SUMMARY OF THE INVENTION

The present invention relates to methods for determining if a pregnant woman is at risk of developing preeclampsia. In certain embodiments, the invention relates to methods for determining if a pregnant woman has preeclampsia.

In one embodiment, the subject invention relates to a method for determining if a pregnant woman is at risk of developing preeclampsia, comprising: (a) culturing human trophoblast cells in the presence of serum or plasma from a pregnant woman; (b) culturing an equivalent sample of human trophoblast cells under the same conditions as cells in (a) but in the absence of serum or plasma from a pregnant woman; and (c) comparing viability of cells cultured in (a) with the viability of cells cultured in (b). If fewer cells cultured in (a) are viable than cells cultured in (b), then the woman is determined to be at risk of developing preeclampsia. "Equivalent samples" include substantially the same number of cells as a sample to which it is being compared. An equivalent sample of trophoblast cells in (b) is a sample of trophoblast cells that includes substantially the same number of trophoblast cells as in the sample cultured in (a). The serum or plasma can be obtained from the pregnant woman at the time the method is carried out (at the time the risk is to be determined) or prior to that time (e.g., it may be obtained, stored and/or shipped to another location before the method is carried out). Optionally, the pregnant woman is to be assessed for risk of developing preeclampsia. In certain embodiments, the pregnant woman is in the first trimester of pregnancy. In certain embodiments, the pregnant woman is in the second trimester of pregnancy. In certain embodiments, the pregnant woman is in the third trimester of pregnancy. In certain embodiments, the invention further comprises (d) culturing an equivalent sample of human trophoblast cells under the same conditions as cells in (a) but in the presence of serum or plasma obtained from a normal control; and (e) comparing viability of cells cultured in (d) with the viability of cells cultured in (a), wherein if fewer cells cultured in (a) than cells cultured in (d) are viable, the woman is determined to be at risk of developing preeclampsia. As used herein, a "normal control" is a (one or more than one) pregnant woman who remains normotensive throughout the gestation. In all instances (e.g., serum or plasma from a pregnant woman or normal control), the serum or plasma from the pregnant woman or normal control can be obtained at the time the method is carried out (at the time the risk is to be determined) or prior to that time (e.g., it may be obtained, stored and/or shipped to another location before the method is carried out).

In one embodiment, the subject invention relates to a method for determining if a pregnant woman is at risk of developing preeclampsia, comprising: (a) culturing human trophoblast cells in the presence of serum or plasma from a pregnant woman; (b) culturing an equivalent sample of human trophoblast cells under the same conditions as cells in (a) but in the absence of serum or plasma from a pregnant woman; and (c) comparing viability of cells cultured in (a) with the viability of cells cultured in (b). If fewer cells cultured in (a) are viable than cells cultured in (b), then the woman is determined to be at risk of developing preeclampsia. Optionally, the pregnant woman is to be assessed for risk of developing preeclampsia. In certain embodiments, the pregnant woman is in the first trimester of pregnancy. In certain embodiments, the pregnant woman is in the second trimester of pregnancy. In certain embodiments, the pregnant woman is in the third trimester of pregnancy. In certain embodiments, the invention further comprises (d) determining if cells cultured in (a) undergo apoptosis; and (e) determining if cells cultured in (b) under apoptosis, wherein if more cells cultured in (a) undergo apoptosis than cells cultured in (b), then the woman is determined to be at risk of developing preeclampsia. Optionally, the apoptosis is determined by detecting an apoptotic marker. In certain embodiments, the apoptotic marker is active caspase-3. In one embodiment, the active caspase-3 is selected from p17 and p19.

In another embodiment, the present invention relates to a method for determining if a pregnant woman has preeclampsia, comprising: (a) culturing human trophoblast cells in the presence of serum or plasma from a pregnant woman; (b)

culturing an equivalent sample of human trophoblast cells under the same conditions as cells in (a) but in the absence of serum or plasma from a pregnant woman; and (c) comparing viability of cells cultured in (a) with the viability of cells cultured in (b). If fewer cells cultured in (a) are viable than cells cultured in (b), then the woman is determined to have preeclampsia. Optionally, the pregnant woman is to be assessed for having preeclampsia. In certain embodiments, the invention further comprises (d) culturing an equivalent sample of human trophoblast cells under the same conditions as cells in (a) but in the presence of serum or plasma obtained from a normal control; and (e) comparing viability of cells cultured in (d) with the viability of cells cultured in (a), wherein if fewer cells cultured in (a) than cells cultured in (d) are viable, the woman is determined to have preeclampsia.

In another embodiment, the present invention relates to a method for determining if a pregnant woman has preeclampsia, comprising: (a) culturing human trophoblast cells in the presence of serum or plasma from a pregnant woman; (b) culturing an equivalent sample of human trophoblast cells under the same conditions as cells in (a) but in the absence of serum or plasma from a pregnant woman; and (c) comparing viability of cells cultured in (a) with the viability of cells cultured in (b). If fewer cells cultured in (a) are viable than cells cultured in (b), then the woman is determined to have preeclampsia. Optionally, the pregnant woman is to be assessed for having preeclampsia. In certain embodiments, the invention further comprises (d) determining if cells cultured in (a) undergo apoptosis; and (e) determining if cells cultured in (b) under apoptosis, wherein if more cells cultured in (a) undergo apoptosis than cells cultured in (b), then the woman is determined to have preeclampsia. Optionally, the apoptosis is determined by detecting an apoptotic marker. In certain embodiments, the apoptotic marker is active caspase-3. In one embodiment, the active caspase-3 is selected from p17 and p19.

In further embodiments, the invention relates to a method for determining if a pregnant woman is at risk of developing preeclampsia, comprising: (a) culturing human trophoblast cells in the presence of (i) anti-Fas antibodies and (ii) serum or plasma obtained from a pregnant woman; (b) culturing an equivalent sample of human trophoblast cells under the same conditions as cells in (a) but in the absence of serum or plasma obtained from a pregnant woman; and (c) comparing viability of cells cultured in (a) with the viability of cells cultured in (b). If fewer cells cultured in (a) are viable than cells cultured in (b), then the woman is determined to be at risk of developing preeclampsia. Optionally, the pregnant woman is to be assessed for risk of developing preeclampsia. In certain embodiments, the anti-Fas antibodies are cultured with the cells independently of the serum or plasma. In certain embodiments, the invention further comprises (d) culturing an equivalent sample of human trophoblast cells under the same conditions as cells in (a) but in the presence of serum or plasma obtained from a normal control; and (e) comparing viability of cells cultured in (d) with the viability of cells cultured in (a), wherein if fewer cells cultured in (a) than cells cultured in (d) are viable, the woman is determined to be at risk of developing preeclampsia.

In further embodiments, the invention relates to a method for determining if a pregnant woman is at risk of developing preeclampsia, comprising: (a) culturing human trophoblast cells in the presence of (i) anti-Fas antibodies and (ii) serum or plasma obtained from a pregnant woman; (b) culturing an equivalent sample of human trophoblast cells under the same conditions as cells in (a) but in the absence of serum or plasma obtained from a pregnant woman; and (c) comparing viability of cells cultured in (a) with the viability of cells cultured in (b). If fewer cells cultured in (a) are viable than cells cultured in (b), then the woman is determined to be at risk of developing preeclampsia. Optionally, the pregnant woman is to be assessed for risk of developing preeclampsia. In certain embodiments, the anti-Fas antibodies are cultured with the cells independently of the serum or plasma. In certain embodiments, the invention further comprises (d) determining if cells cultured in (a) undergo apoptosis; and (e) determining if cells cultured in (b) under apoptosis, wherein if more cells cultured in (a) undergo apoptosis than cells cultured in (b), then the woman is determined to be at risk of developing preeclampsia. Optionally, the apoptosis is determined by detecting an apoptotic marker. In certain embodiments, the apoptotic marker is active caspase-3. In one embodiment, the active caspase-3 is selected from p17 and p19.

In further embodiments, the invention relates to a method for determining if a pregnant woman has preeclampsia, comprising: (a) culturing human trophoblast cells in the presence of (i) anti-Fas antibodies and (ii) serum or plasma obtained from a pregnant woman; (b) culturing an equivalent sample of human trophoblast cells under the same conditions as cells in (a) but in the absence of serum or plasma obtained from a pregnant woman; and (c) comparing viability of cells cultured in (a) with the viability of cells cultured in (b). If fewer cells cultured in (a) are viable than cells cultured in (b), then the woman is determined to have preeclampsia. Optionally, the pregnant woman is to be assessed for having preeclampsia. In certain embodiments, the anti-Fas antibodies are cultured with the cells independently of the serum or plasma. In certain embodiments, the invention further comprises (d) culturing an equivalent sample of human trophoblast cells under the same conditions as cells in (a) but in the presence of serum or plasma obtained from a normal control; and (e) comparing viability of cells cultured in (d) with the viability of cells cultured in (a), wherein if fewer cells cultured in (a) than cells cultured in (d) are viable, the woman is determined to have preeclampsia.

In further embodiments, the invention relates to a method for determining if a pregnant woman has preeclampsia, comprising: (a) culturing human trophoblast cells in the presence of (i) anti-Fas antibodies and (ii) serum or plasma obtained from a pregnant woman; (b) culturing an equivalent sample of human trophoblast cells under the same conditions as cells in (a) but in the absence of serum or plasma obtained from a pregnant woman; and (c) comparing viability of cells cultured in (a) with the viability of cells cultured in (b). If fewer cells cultured in (a) are viable than cells cultured in (b), then the woman is determined to have preeclampsia. Optionally, the pregnant woman is to be assessed for having preeclampsia. In certain embodiments, the anti-Fas antibodies are cultured with the cells independently of the serum or plasma. In certain embodiments, the invention further comprises (d) determining if cells cultured in (a) undergo apoptosis; and (e) determining if cells cultured in (b) under apoptosis, wherein if more cells cultured in (a) undergo apoptosis than cells cultured in (b), then the woman is determined to have preeclampsia. Optionally, the apoptosis is determined by detecting an apoptotic marker. In certain embodiments, the apoptotic marker is active caspase-3. In one embodiment, the active caspase-3 is selected from p17 and p19.

In further embodiments of the invention, the invention relates to a method for determining if a pregnant woman is at risk of developing preeclampsia, comprising: (a) culturing human trophoblast cells in the presence of serum or plasma obtained from a pregnant woman and (b) determining if cells cultured in (a) undergo apoptosis, wherein if cells cultured in (a) undergo apoptosis, the woman is determined to be at risk of developing preeclampsia. In certain embodiments, the pregnant woman is in the first trimester of pregnancy. In certain embodiments, the pregnant woman is in the second trimester of pregnancy. In certain embodiments, the pregnant woman is in the third trimester of pregnancy. Optionally, the apoptosis is determined by detecting an apoptotic marker. In certain embodiments, the apoptotic marker is active caspase-3. In one embodiment, the active caspase-3 is selected from p17 and p19. In certain embodiments, the invention further comprises (c) culturing an equivalent sample of human trophoblast cells under the same conditions as cells in (a) but in the presence of serum or plasma obtained from a normal control; and (d) determining if the cells cultured in (c) undergo apoptosis, wherein if more cells cultured in (a) undergo apoptosis than cells cultured in (c), the woman is determined to be at risk of developing preeclampsia.

Kits for determining if a pregnant woman is at risk of developing preeclampsia are also the subject of this invention. In one embodiment, such a kit comprises trophoblast cells, growth media, and a container for culturing trophoblast cells. In a further embodiment, the trophoblast cells are immortalized trophoblast cells. In an additional embodiment, the trophoblast cells are H8 trophoblast cells. The kits of the invention can further include instructions for use.

BRIEF DESCRIPTION OF THE DRAWINGS

FIG. 3 is a table depicting the patient characteristics relating to the data presented in FIGS. 4-6.

DETAILED DESCRIPTION OF THE INVENTION

Figure 1:
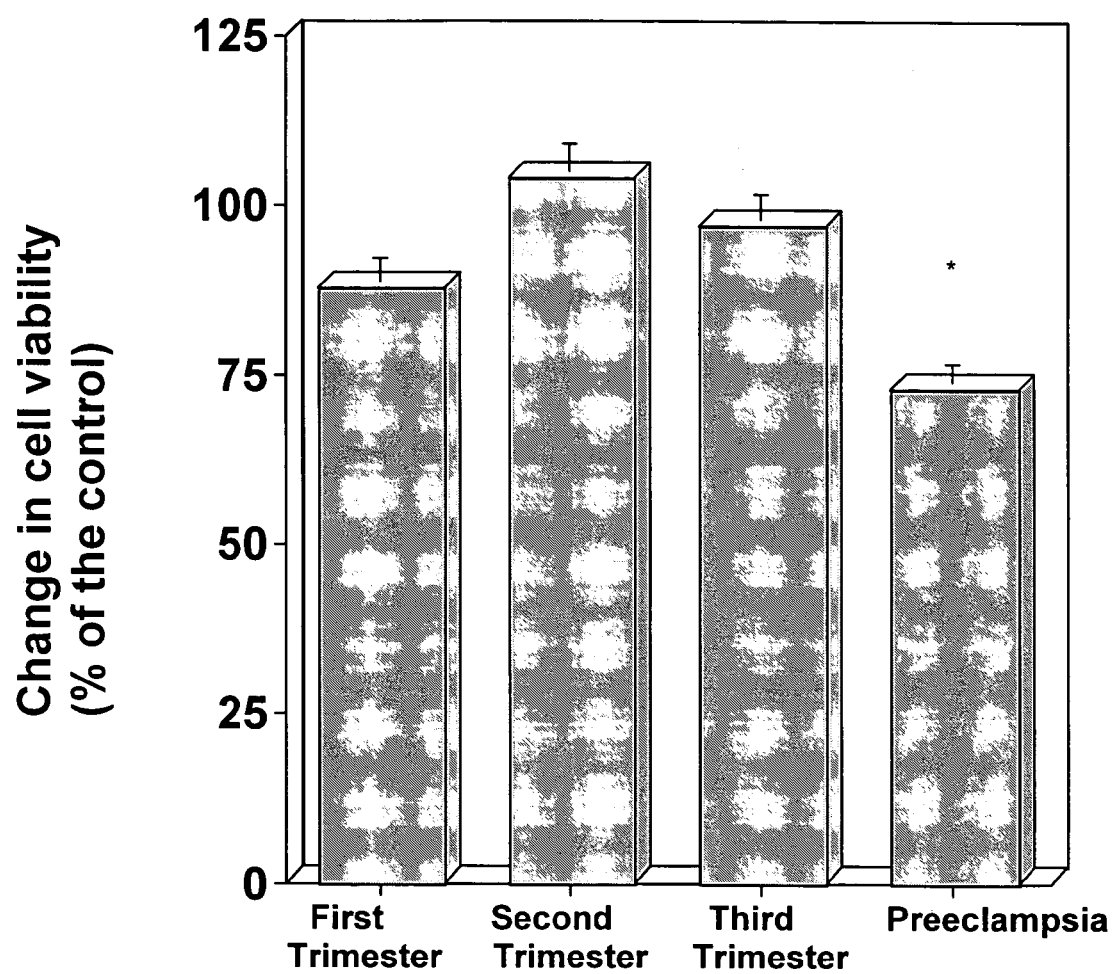
FIG. 1 is a graph depicting the effect of normal and preeclamptic serum on trophoblast cell viability.

Described herein are methods for determining if a pregnant woman is at risk of developing preeclampsia. Also described herein are methods for determining if a pregnant woman has preeclampsia.

The term "preeclampsia" includes a hypertensive, multi-system disorder of pregnant women, characterized by hypertension, proteinuria, and edema. The most common symptoms of preeclampsia are high blood pressure, increased protein in the urine, and swelling or edema of hands and feet. In specific embodiments of the present invention, preeclampsia is defined as hypertension (systolic blood pressure $\geq 140$ mmHg or diastolic blood pressure $\geq 90$ mmHg on at least two occasions, 4 hours to 1 week apart) and proteinuria (>300 milligrams in a 24 hour urine collection or one dipstick measurement >2+).

The methods of the invention employ trophoblast cells. In certain embodiments, the trophoblast cells are immortalized trophoblast cells. For example, immortalized trophoblast cells for use in the methods of the subject invention include H8 trophoblast cells. Cells used in the invention can be cultured under standard conditions known in the art (e.g., baseline conditions as described in the Examples). In certain embodiments, trophoblast cells used in the invention are cultured under conditions as provided in the Examples.

The present invention provides methods for the detection of patients at risk of developing preeclampsia. The present invention also relates to methods for the detection of patients with preeclampsia. As described herein, a patient is a woman who is pregnant. The subject invention is useful to assess, for a woman in need thereof, the risk of developing preeclampsia or whether, for a woman in need thereof, a woman has preeclampsia.

The methods of the present invention employ serum or plasma obtained from a pregnant woman. In certain embodiments of the invention, trophoblast cells are contacted with serum or plasma obtained from a (one or more than one) pregnant woman, e.g., by culturing trophoblast cells in the presence of serum or plasma obtained from a pregnant woman. In certain embodiments of the present invention, serum or plasma is obtained from a pregnant woman once during the course of the pregnancy. Optionally, serum or plasma is obtained from a pregnant woman more than once during the course of the pregnancy. The serum or plasma for use in embodiments of the subject invention may be obtained from a pregnant woman during the first, second, or third trimester of pregnancy or any combination thereof (e.g., first and third trimesters; e.g., second and third trimesters; e.g., first and second trimesters; e.g., first, second and third trimesters).

The present invention also relates to assessing the viability of trophoblast cells. Cell viability can be assessed by any means known in the art. For example, cell viability may be assessed by a cell proliferation assay such as the CellTiter 96® AQueous One Solution Cell Proliferation Assay (Promega, Madison, Wis.). This assay is a calorimetric method for determining the number of viable cells in proliferation, cytotoxicity or chemosensitivity assays. The CellTiter 96® AQueous One Solution Reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). Assays are performed by adding a small amount of the CellTiter 96® AQueous One Solution Reagent directly to culture wells, incubating for 1-4 hours and then recording absorbance at 490 nm with a 96-well plate reader. The quantity of formazan product as measured by the amount of 490 nm absorbance is directly proportional to the number of living cells in culture.

The present invention further relates to assessing whether trophoblast cells undergo apoptosis. One apoptosis assay that may be used in embodiments of the subject invention is a caspase-3 assay, in which caspase-3 activity is measured using a colorimetric substrate. For example, cleavage of the substrate Ac-DEVD-pNA by caspase-3 releases pNA (p-nitroaniline), which produces a yellow color that can be monitored by a spectrophotometer at 405 nm. The amount of yellow color produced upon cleavage is proportional to the amount of caspase-3 activity.

In certain embodiments of the present invention, apoptosis of trophoblast cells is determined by detection of an apoptotic marker. An apoptotic marker or indicator includes, for example, radioactive molecules, fluorescent molecules, and enzymatic molecules that are associated with apoptotic cell death. For example, apoptotic markers include active caspase-3, e.g., caspase-3 p17 and p19 fragments. Another apoptosis assay that may be used to assess trophoblast cell death is the TUNEL assay, which is used to detect the presence of apoptotic cell death. In the TUNEL assay, the enzyme terminal deoxynucleotidyl transferase labels 3'-OH DNA ends (which are generated during apoptosis) with biotinylated nucleotides. The biotinylated nucleotides are then detected by immunoperoxidase staining. In further embodiments, apoptotic features such as cell shrinkage, chromatin condensation, and DNA fragmentation may be detected as indicators of apoptosis.

In another embodiment, the invention relates to kits useful for the prediction and detection of preeclampsia. The kits of the invention comprise trophoblast cells, media suitable for culturing trophoblast cells, and containers for carrying out the methods of the present invention. Containers that may be employed in the subject invention include any container suitable for carrying out the invention, for example, a container suitable for use in the present invention is a well such as a microtiter-plate well. In certain embodiments, the kits of the invention include instructions for carrying out the present invention.

The hallmark of normal placentation is the invasion of trophoblast cells into the decidual and myometrial segments of the spiral arteries, resulting in the reversible obliteration of the normal arterial wall architecture (3). Muscular, medial elastic, and endothelial layers of the arteriolar walls are invaded by trophoblasts and replaced by fibrinoid material, converting narrow-lumen spiral arteries into large-bore uteroplacental vessels (4). In contrast, failure of physiologic transformation of the myometrial segment of the spiral arteries is characteristic of abnormal placentation and has been considered central to the pathophysiology of preeclampsia for the past 30 years (5, 3, 6). Moreover, recent microscopic studies of placental specimens from women with preeclampsia have demonstrated that the extra villous trophoblasts anchoring the placenta to the uterine wall show marked apoptosis as early as the first trimester (7, 8), suggesting that the initial insult occurs early in gestation and may involve the trophoblast (9, 10, 11).

Around the second postconceptional week, the cytotrophoblast and syncytiotrophoblast differentiate from the implanted blastocyst (47). The cytotrophoblast divides to form syncytiotrophoblasts and further proliferates to form a specialized trophoblast referred to as an extravillous trophoblast. It is the extravillous trophoblast that extends through the endometrium to reach the border of the decidua and myometrium. The extravillous trophoblast continues its invasion into the spiral arterioles and replaces the endothelial and muscular linings of the uterine arterioles, leading to vasodilation of the uterine vasculature (7). This change ensures a continued low resistance system, which potentiates maternal blood flow to the intervillous space and maintains adequate perfusion of the developing fetus.

In preeclampsia, with the absence of marked vasodilation and with the lumen of the vessels essentially occluded, blood flow and oxygen transfer to the fetus is diminished leading to the maternal manifestations of preeclampsia as well as the fetal manifestations of oligohydramnios and intrauterine growth restriction (IUGR). One theory to explain the etiology of preeclampsia implicates an injured placenta leading to hypoperfusion of the implantation site and endothelial cell damage (48). This local endothelial cell damage in turn leads to systemic endothelial cell dysfunction. The initial injury to the placenta may be a result of increased cell death or apoptosis of the extravillous trophoblast.

Apoptosis is an adaptive process which balances cell growth and death to maintain tissue homeostasis. Many genes are involved in the control of apoptosis. The Fas/Fas Ligand (Fas/FasL) system is one of the main apoptotic pathways. The Fas/FasL system is expressed in immune as well as non-immune cells such as trophoblasts (50). Its expression and function responds to changes in the microenvironment, playing a pivotal role in controlling cell proliferation and tissue remodeling (22, 23). Both FasL and Fas are transmembranous proteins of the TNF-α/TNFα-receptor family. The binding of the Fas receptor by FasL results in a downstream activation of a cascade of intracellular proteolytic enzymes ending in apoptosis (51).

Although cytotrophoblast cells from normal pregnancies express Fas and FasL, they are resistant to Fas mediated apoptosis (19, 52). Furthermore, it has been demonstrated that this resistance to Fas—mediated apoptosis is in part dependent on the cytokine profile at the implantation site (19). Applicants hypothesize that changes in the normal microenvironment at the implantation site may influence trophoblast sensitivity to apoptosis, which may then lead to placental damage, impaired trophoblast invasion and pathological conditions such as preeclampsia.

In certain embodiments, the present invention relates to a cytotoxic assay comprising trophoblast cells treated with sera from women with normal pregnancies and pregnancies complicated by preeclampsia. Further, Applicants have demonstrated a differential effect of sera from preeclamptic patients and normal patients on trophoblast cell viability and sensitivity to Fas-mediated apoptosis.

Lately, attention has turned to the role of apoptosis in normal tissue remodeling of the female reproductive tract and the effect of excessive apoptosis in degenerative diseases such as preeclampsia, IUGR and preterm labor (12, 13). Apoptosis within the pregnant uterus is important for the establishment of immune privilege, as well as the regulation of placental growth (14, 15). However, excessive trophoblast apoptosis may affect placental function, resulting in adverse perinatal outcome. Increased trophoblast apoptosis has been documented in the placenta of growth-restricted fetuses (16), recurrent spontaneous abortion (17), preeclamptic pregnancy, and post-term pregnancy (18). The balance between cell proliferation and cell death is determined by factors produced at the maternal-fetal interface or by the maternal circulation (19).

Another area of study has focused on the importance of the trophoblast in the pathophysiology of preeclampsia. Specifically, deportation of villous trophoblast debris directly into the maternal circulation (39, 40, 41) has been implicated in the genesis of the exaggerated intravascular maternal inflammatory response noted in patients with preeclampsia. In addition, increased apoptosis of villous and extra villous trophoblasts has been reported in cases of preeclampsia (42, 43).

Applicants hypothesized that the factors regulating trophoblast survival are present in maternal serum, may be detected early in pregnancy and can be evaluated in vitro. Applicants demonstrate that serum from women destined to develop preeclampsia significantly reduced trophoblast cell viability. Furthermore, this effect on cell viability is apparent as early as the first trimester. In addition, this effect is related to the activation of the apoptotic cascade in trophoblast cells. This finding is consistent with the hypothesis that the initiating cellular events leading to preeclampsia occur early in pregnancy and certainly before the development of clinical signs of the disease.

Applicants suggest that there is a link between maternal serum factors and trophoblast apoptosis. Applicants demonstrate that serum from women with preeclampsia increases trophoblast sensitivity to Fas-mediated apoptosis (20). Although the magnitude is different, the effect on trophoblast cell viability observed in active pre-eclamptic cases is similar to that seen when trophoblast cells are exposed to the "pre-disease" sera. Interestingly, the "pre-disease" sera induced a greater decrease in cell viability than that induced by sera from women with active disease. Hence, instead of a pressor agent being responsible for the initiation of preeclampsia, as previously believed, other factor(s), such as pro-inflammatory cytokine(s), may initiate an abnormally high rate of trophoblast apoptosis (44).

This increased trophoblast apoptosis may in turn lead to defective placental function. It has been shown that the pro-inflammatory cytokines TNF-α and IFN-γ increase trophoblast sensitivity to apoptotic stimuli, whereas anti-inflammatory cytokines, including IL-10, protect trophoblast cells from apoptosis by up-regulating anti-apoptotic proteins such as FLIP (14, 19). Work described herein indicates a role for apoptosis in the pathophysiology of trophoblast diseases such as preeclampsia and IUGR.

A significant decrease in trophoblast viability was observed with sera from women who subsequently developed preeclampsia (24% vs. 4% p=0.013) and was associated with caspase-3 activation. Accordingly, factors capable of inducing trophoblast apoptosis are present in the patients' sera weeks or months before the clinical development of the disease. The invention described herein is useful to identify women at risk of preeclampsia.

In one embodiment of the present invention, the invention relates to the study of apoptosis in preeclampsia as a marker for the onset of the disease. In one embodiment, the present invention can be utilized as a sensitive assay to screen for patients at risk of developing preeclampsia. In certain embodiments, the sensitivity of this assay is 81%, and the specificity 66%, wherein a "positive test" is defined by a reduction in trophoblast viability greater than 10%. In one embodiment, a pregnant woman is diagnosed as being at risk of developing preeclampsia when there is a greater than 10% reduction in trophoblast viability as assessed by the methods of the present invention. For example, in certain embodiments, if there is a greater than 10% reduction in viability of trophoblast cells cultured in the presence of serum from a pregnant woman when compared to the viability of trophoblast cells cultured in the absence of serum from the pregnant woman, then the woman is determined to be at risk for developing preeclampsia. By assessing large numbers of patients, the sensitivity and specificity of the assays of the subject invention can be increased.

An advantage of the present invention is the fact that the predictability of disease is not confined to the 3rd trimester. Applicants were able to show differential effects of sera obtained as early as 6 weeks of gestation on trophoblast cell viability. Although not all patients at risk for developing preeclampsia enter prenatal care in the first trimester, the subject invention can be used since a reduction in trophoblast viability was observed in the pre-disease group, regardless of which trimester the serum sample was obtained.

Applicants suggest a potential link between serum factor (s) and trophoblast viability. This factor(s) may be responsible for changes in the normal microenvironment at the implantation site, which may have a direct effect on trophoblast viability, leading to impaired trophoblast function and invasion. Regardless of the specific nature of this factor(s), it appears that it is present and active several weeks before patients show clinical signs/symptoms of preeclampsia.

The practice of the present invention will employ, unless otherwise indicated, conventional techniques of cell biology, cell culture, molecular biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999.

EXEMPLIFICATION

The invention now being generally described, it will be more readily understood by reference to the following examples, which are included merely for purposes of illustration of certain aspects and embodiments of the present invention, and are not intended to limit the invention.

Example 1

Methods

Cells

First trimester H8 trophoblast cell line was maintained in RPMI supplemented with 10% Fetal Bovine Serum (FBS) (Gemini Bioproducts), 1000 units/ml penicillin, 100 g/ml streptomycin, 10 mM HEPES, 100 nM non-essential amino acids and 1 mM sodium pyruvate (Gibco, Carlsbad, Calif.), at 37° C./5% $CO_2$.

Blood Samples

Blood samples were obtained from normal patients in the first (18), second (19), and third trimester (11), and 12 preeclamptic patients. Pregnancies were considered normal when medical and obstetrical complications of pregnancy were ruled out and birthweight was appropriate-for-gestational-age at term ($\geq$37 gestational weeks). Preeclampsia was defined as hypertension (systolic blood pressure $\geq$140 mmHg or diastolic blood pressure $\geq$90 mmHg on at least two occasions, 4 hours to 1 week apart) and proteinuria (>300 milligrams in a 24 hour urine collection or one dipstick measurement >2+)(21). The medical records of all of the normal control patients were reviewed to confirm that no one had antepartum, intrapartum or postpartum complications. Patients with chronic hypertension, diabetes mellitus, antiphospholipid antibody syndrome, thrombophilic mutations or transient blood pressure elevations were excluded from this study. Approval for this study was obtained through the Human Investigations Committee at Yale University and NICHD.

Cytotoxic Assay

For the cytotoxic assay, 5,000H8-trophoblast cells/well were plated in a 96 well plate in complete media. Afterwards, cells were incubated in Optimem, (without serum) for 24 hours, thereafter treated with serum from the patients at 10% final concentration in Optimem for 48 hours at 37° C.

Cell viability was assessed with the Cell Titer 96 Aqueous One Solution Cell Proliferation Assay (Promega). This assay is a colorimetric method for determining the number of viable cells in culture. It utilizes 3-(4,5-dimethylthiazol-2-yl)-5-(3-carboxymethoxyphenyl)-2-(4-sulfophenyl)-2H-tetrazolium (MTS) that is bioreduced by cells into a colored formazan product. NADPH accomplishes this conversion or NADH produced by dehydrogenase enzymes in metabolically active cells (53). Thus, the quantity of formazan product, as measured by the amount of absorbance at 490 nm, is directly proportional to the number of living cells in culture. The data is presented as percent viability, which is calculated by subtracting the amount of viable cells in the experimental condition (e.g., trophoblast cells cultured in the presence of serum from a pregnant woman), from the amount of viable cells in the baseline condition (e.g., an equivalent sample of trophoblast cells cultured in the absence of serum from a pregnant woman), divided by the amount of viable cells in the baseline condition, multiplied by 100% (23).

Sensitivity to Fas-mediated Apoptosis

In addition to the serum from normal pregnant controls or from preeclamptic cases, the first trimester H 8 trophoblast cells were treated with an agonist anti Fas antibody or a blocking anti FasL antibody. Anti Fas antibody mimics FasL and promotes apoptosis, while anti-FasL antibody blocks the receptor and inhibits apoptosis. Cell viability was assessed with the Cell Titer 96 Aqueous One Solution Cell Proliferation Assay (Promega). Cell viability was expressed as percentage of the control as described above.

Statistical Analysis

The data were tested for statistical significance by the ANOVA; Bonferroni comparison of means and student t test where appropriate. A p value of <0.05 was considered significant.

Results

Effect of Normal Serum from Each Trimester on Trophoblast Cell Viability

To characterize the effect of normal serum obtained from first, second and third trimesters of pregnancy on trophoblast cell viability, Applicants developed a cytotoxicity assay comprising first trimester H-8 trophoblast cells incubated for 48 hours with the patients' serum. Serum obtained from the first trimester of normal pregnancy induced a 12% reduction in cell viability compared to base line conditions. A 4% increase in cell viability was observed when the trophoblast were exposed to 2nd trimester sera, and a 3% decline in cell viability was seen when 3rd trimester sera were used.

Effect of Serum from Preeclamptic Patients on Trophoblast Viability

Applicants then evaluated the effect of serum obtained from patients with the diagnosis of preeclampsia on trophoblast cell viability. Thus, when the trophoblast cells were exposed to serum from women with preeclampsia, there was a 27% decline in cell viability. This was a significant difference from the normal pregnancy control group (p=0.014; FIG. 1).

Effect of Serum from Preeclamptic Patients on Fas-mediated Apoptosis

Figure 2:
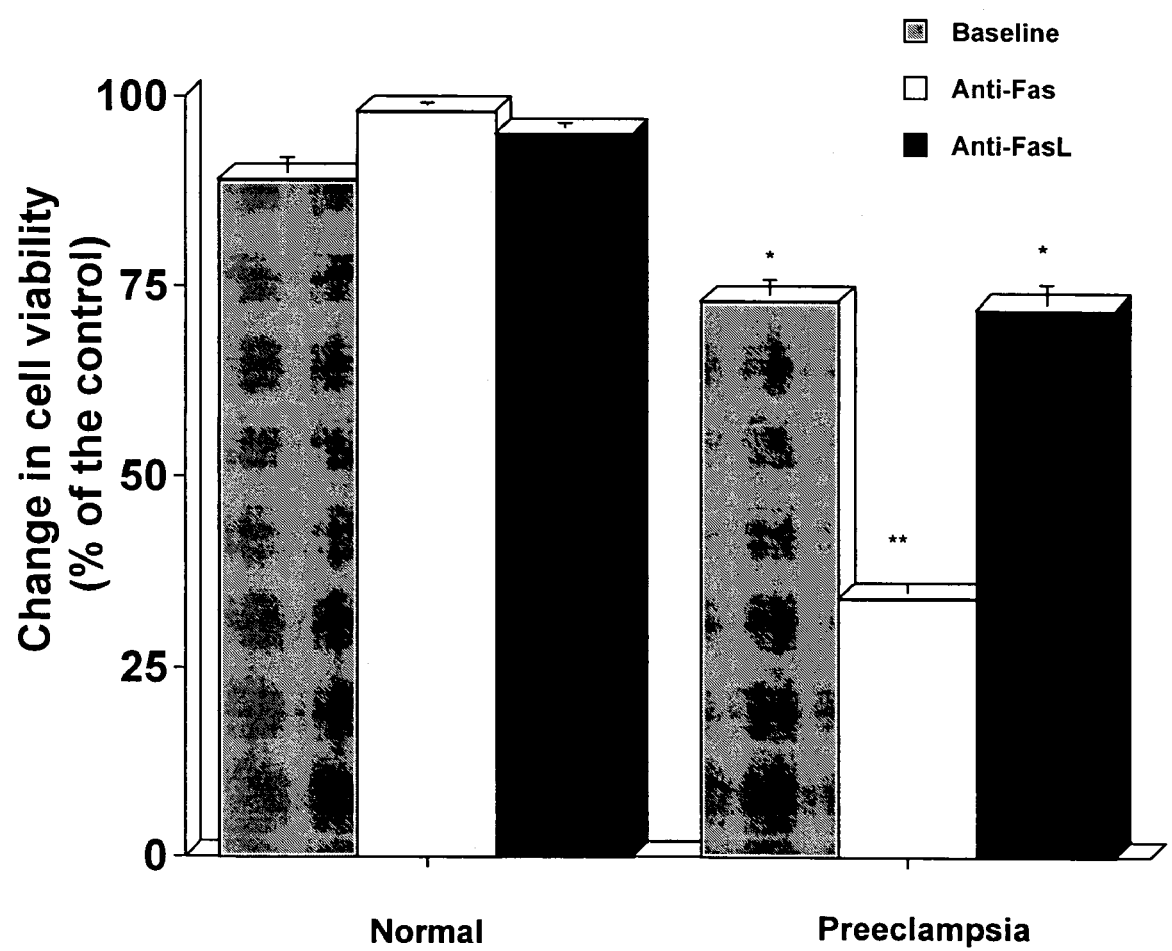
FIG. 2 is a graph depicting the effect of serum from preeclamptic patients on Fas-mediated apoptosis.

In order to elucidate whether the decrease on trophoblast cell viability induced by serum from preeclamptic patients involves Fas-mediated apoptosis, cells were treated during the incubation period with an anti Fas antibody, which mimics FasL and promotes apoptosis, or a blocking anti FasL antibody that blocks the interaction of FasL with Fas and therefore inhibits Fas-mediated apoptosis. In the normal pregnancy control group, the addition of anti Fas or Anti FasL antibodies produced no effect on trophoblast cell viability. In contrast, the addition of anti Fas antibody to the preeclamptic sera further increased cell death to 35% reduction in trophoblast viability compared to the normal (p=0.022). No effect was found following treatment with the anti-FasL antibody. (FIG. 2).

Discussion

Applicants describe a cytotoxic effect of preeclamptic serum on first trimester trophoblast cells. Furthermore, Applicants show that this effect may be related to changes in trophoblast sensitivity to Fas mediated apoptosis.

Apoptosis is an adaptive process to balance cell growth and death, and restore homeostasis. During early pregnancy, the trophoblast is in general resistant to apoptosis allowing the growth and normal invasion of the placenta. Some studies suggest that placental apoptosis may increase as pregnancy progresses. Dysregulation of apoptosis may be related to pathologic conditions such as preeclampsia, intrauterine growth restriction, and possibly pre-term labor (54-56). It has recently been shown that there is increased apoptosis in placental beds of pregnancies complicated by preeclampsia (57).

Applicants have shown a differential effect of serum from normal pregnancies and preeclamptic pregnancies on trophoblast cell viability. While normal serum did not induce significant changes in cell viability, serum from preeclamptic patients had a cytotoxic effect on trophoblast cells. This finding suggests the presence of factor(s) affecting the regulation of apoptosis. Some of these toxic factors may be related to cytokines, which can induce activation of apoptotic genes and promote cell death. Thus, preeclampsia has been related to increase in proinflammatory cytokines such as TNF-$\alpha$, IL-1, IFN$\gamma$, and IL-6 (54, 58, 59). These cytokines have been shown to activate apoptotic genes such as the Fas/FasL system (19) and bcl2 family (57) in trophoblast, leading to aberrant placental invasion, function, and rejection.

It has been demonstrated that anti-inflammatory cytokines increase the resistance of trophoblast cells to Fas-mediated apoptosis, either by inhibiting Fas expression or inducing FLIP activation. On the other hand, pro-inflammatory cytokines increase trophoblast sensitivity to Fas-mediated apoptosis (19). Applicants have found that serum from preeclamptic patients render the trophoblast more sensitive to Fas mediated apoptosis, suggesting the presence of high levels of proinflammatory cytokines.

An important cellular component in preeclampsia is the presence of high levels of activated neutrophils, which constitutes a potential source of pro-inflammatory cytokines, creating a pro-apoptotic milieu at the maternal-fetal interface (60-63).

Applicants suggest that changes in the normal microenvironment at the implantation site influence trophoblast sensitivity to apoptosis, which then may lead to placental damage, impaired trophoblast invasion and pathological conditions such as preeclampsia. The present invention demonstrates a potential link between systemic serum factor(s) and their local effect on trophoblast cell viability. Although the systemic cytotoxic factors have not yet been identified, clearly the differential effect of serum from normal versus preeclamptic patients on trophoblast viability suggests their presence.

Example 2

Applicants investigated whether the sera of women who subsequently develop preeclampsia have a pro-apoptotic effect on trophoblasts.

Study Design

Serum samples were obtained from 96 pregnant women. Fifty-eight samples (28 first trimester, 19 second trimester, 11 third trimester) were obtained from women who remained normotensive throughout the gestation (herein referred to as normal). Thirty-eight samples (14 first trimester, 18 second trimester, 6 third trimester) were from women who were normotensive at the time that the serum samples were obtained and who subsequently developed preeclampsia (herein referred to as pre-disease). Preeclampsia was defined as hypertension (systolic blood pressure $\geq$140 mmHg or diastolic blood pressure ≧90 mmHg on at least two occasions, 4 hours to 1 week apart) and proteinuria (>300 milligrams in a 24 hour urine collection or one dipstick measurement >2+)(21). The medical records of all of the normal control patients were reviewed to confirm that none of them had antepartum, intrapartum or postpartum complications. Patients with chronic hypertension, diabetes mellitus, antiphospholipid antibody syndrome, thrombophilic mutations or transient blood pressure elevations were excluded. The use of these samples for research purposes was approved by the Human Investigation Committee at Yale University and the NICHD IRB.

Cell Viability Assay

The first trimester human trophoblast cell line, H8, was maintained in RPMI supplemented with 10% FBS (Gemini Bioproducts), 1000 U/ml penicillin, 100 µg/ml streptomycin, 10 mmol/1 HEPES, 100 mmol/1 non-essential amino acids and 1 mmol/1 sodium pyruvate (Gibco, BRL, Gaithersburg, Md., USA), at 37° C./5% $CO_2$. For the assay, trophoblast cells (5000 cells/well) were plated in a 96 well plate in complete media and grown to 80% confluence. Cells were then incubated in OptiMem (Opti-Merr, Gibco BRL) (without serum) for 24 hours, and thereafter treated with serum obtained from the patients at 10% final concentration in OptiMem for 48 hours at 37° C. Cell viability was assessed with the Cell Titer 96 Aqueous One Solution Cell Proliferation Assay (Promega, Madison, Wis., USA). This assay is a colorimetric method for determining the number of viable cells in culture. It utilizes 3-(4,5-dimethylthiazol-2-yl)-5-(3-carboxymethoxphenyl)-2-(4-sulfophenyl)-2H-tetrazolium (MTS) that is bio-reduced by cells into a colored formazan product. All specimens were run in duplicate and repeated at least two times with similar results. The data are presented as percent viability, which is calculated by subtracting the amount of viable cells in the experimental condition (e.g., trophoblast cells cultured in the presence of serum from a pregnant woman), from the amount of viable cells in the baseline condition (e.g., trophoblast cells cultured in the absence of serum from a pregnant woman), divided by the amount of viable cells in the baseline condition, multiplied by 100% (22).

Effect of Normal and Pre-preeclamptic Serum on Trophoblast Cell Viability

Figure 4:
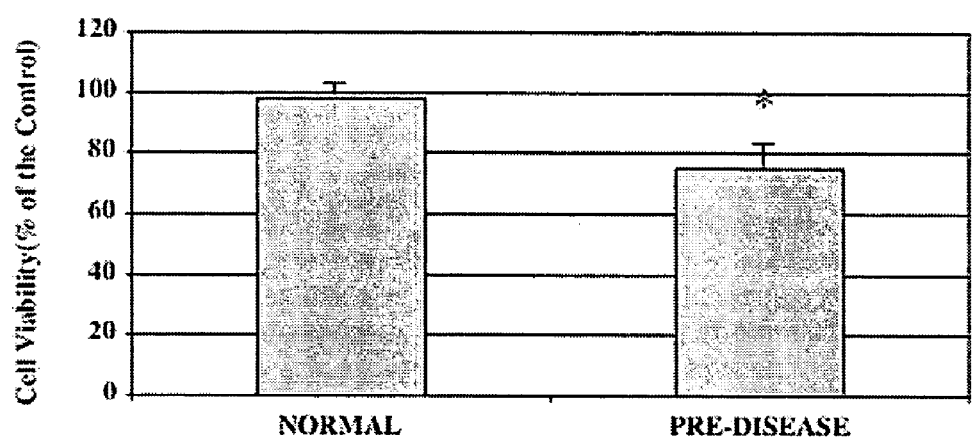
FIG. 4 is a graph depicting the effect of normal and pre-preeclamptic serum on trophoblast cell viability.

The first trimester H8 trophoblast cell line was treated with 10% serum obtained from normotensive women or pre-disease patients in the first, second and third trimesters of pregnancy. Cell viability was determined by the Cell Titer 96 assay. Data are presented as mean±SD percentage of the control (*pre-disease 76%+5% vs. normal pregnancy 97%+4%; p=0.007) (FIG. 4).

Figure 5:
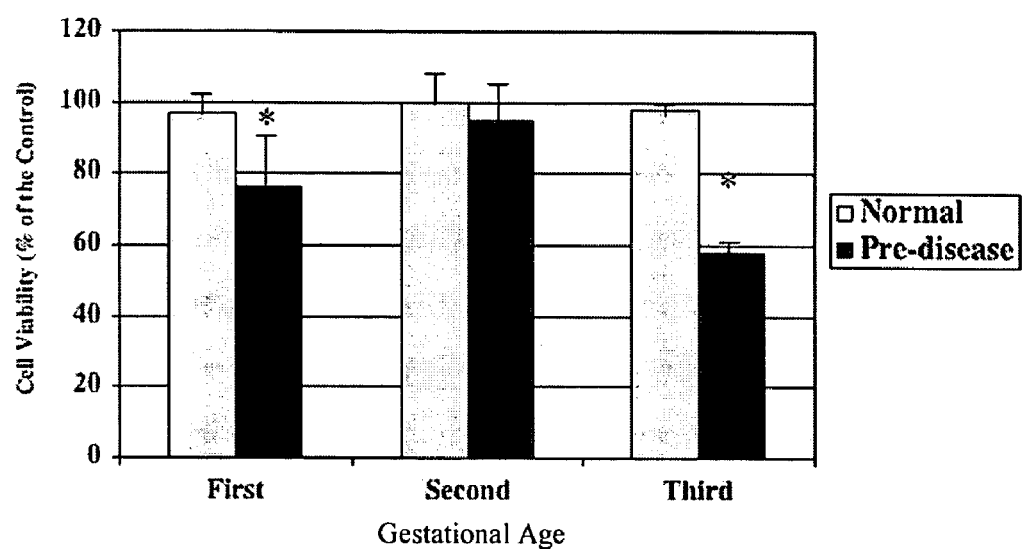
FIG. 5 is a graph depicting the effect of sera from first, second, and third trimester pregnancies on trophoblast cell viability.

Effect of Sera from First, Second and Third Trimester Pregnancies on Trophoblast Cell Viability The first trimester H8 trophoblast cell line was treated with 10% serum obtained from first, second or third trimester of pregnancy of normotensive and pre-disease women. Cell viability was determined by the Cell Titer 96 assay. Data are presented as mean±SD percentage of the control (*p=0.007. **p=0.001) (FIG. 5).

Western Blot Analysis $5 \times 10^5$ cells were plated in 35 $mm^2$ petri dishes (BD Biosciences), grown to 70% confluence, and treated with sera as described above. Following treatment, cells were lysed in 1% NP40 and 0.1% SDS in the presence of 0.2 mg/ml PMSF and a protease inhibitor cocktail (Roche Applied Science, Indianapolis, Ind.) on ice for 20 minutes. Cellular debris was removed by centrifugation at 14,000×g at 4° C. Protein concentrations were determined by BCA assay (Pierce Biotechnology, Rockford, Ill.) and 20 µg of each sample was denatured in sample buffer (2.5% SDS, 10% glycerol, 5% b-mercaptoethanol, 0.15 M Tris (pH 6.8) and 0.01% bromophenol blue) and subjected to 12% SDS-PAGE. Proteins were transferred to PVDF membranes (NEN Life Sciences, Boston, Mass.) at 100V for 105 minutes as previously described (23, 24).

Antibodies and concentrations were as follows: rabbit anti-actin (Sigma, 1:10,000), rabbit anti-proform caspase-3 (Santa Cruz, Santa Cruz Calif. 1:1,000), rabbit anti-cleaved caspase-3 (Cell Signaling, 1:1000). Detection of antibody signals was determined by enhanced chemiluminescence detection of peroxidase conjugated secondary antibodies (Vector). The intensity of the signals were analyzed by densitometry and normalized to the Beta-actin signal using a digital imaging analysis system and ID Image Analysis Software (Kodak Scientific Imaging Systems, Rochester, N.Y.).

Effect of Preeclamptic Sera on Caspase-3 Activation

Figure 6:
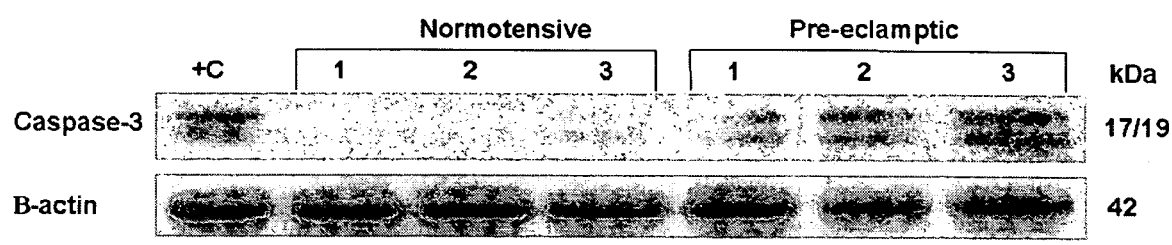
FIG. 6 is a blot depicting the effect of preeclamptic sera on caspase-3 activation.

The first trimester H8 trophoblast cell line was treated with 10% serum obtained from preeclamptic patients for 48 hours. The expression of the active form of caspase-3 was determined by Western blot analysis. Note the presence of the p17 and p19 bands in the trophoblast cells treated with sera from preeclamptic patients, but not in the group treated with sera from normotensive patients (FIG. 6).

Statistical Analysis

The data were tested for statistical significance by the ANOVA, followed by post hoc tests with correction for multiple comparisons and Student t test where appropriate. A p value of <0.05 was considered significant.

Results

Patients Profile

There were no significance differences in maternal age, gravidity or gestational age at serum collection between the two groups. There were more nulliparous women in the pre-disease group and the mean gestational age at which the diagnosis of preeclampsia was determined was 31.4 weeks (FIG. 3).

Pre-disease Serum Reduces Trophoblast Cell Viability

In order to determine if sera from pre-disease patients influences trophoblast survival, Applicants initially evaluated the effect of sera from pre-disease vs. normal pregnancies on trophoblast cell viability. Treatment with serum obtained from pre-disease patients induced a statistically significant decrease in H8 trophoblast cell viability compared to the normal, gestational aged matched controls (24% vs. 4% respectively p=0.007; FIG. 4).

Pre-disease Serum from each Trimester has Differential Effects on Trophoblast Cell Viability Applicants also determined if the effect of pre-disease serum on trophoblast survival was dependent on gestational age. In order to do so, Applicants analyzed the effect of sera obtained from pre-disease and normal patients in the first, second and third trimester of pregnancy. Whereas serum obtained from pre-disease women in the first trimester was associated with a 27% reduction in cell viability (p=0.002; FIG. 5), serum obtained from normal pregnant women in the first trimester showed a 4% reduction in cell viability. Serum obtained from pre-disease women caused an 8% reduction in cell viability (p=0.06; FIG. 5), while serum obtained from normal pregnant women in the second trimester showed a 5% increase in cell viability. Treatment with sera from the pre-disease group in this trimester induced a 41% reduction in cell viability (p=0.001; FIG. 5), whereas serum obtained from normal pregnant women in the third trimester showed a 4% reduction. These results indicate that the decrease in trophoblast cell viability following treatment with pre-disease sera is predominantly detected in the first and third trimester of pregnancy.

Caspase-3 Activation in Trophoblast Cells

In order to determine whether the decrease in trophoblast viability observed in trophoblast cells after treatment with preeclamptic sera was related to the activation of the apoptotic cascade, Applicants evaluated the expression of caspase-3 by Western Blot analysis. As shown in FIG. 6, the active forms of caspase-3 (p19 and p17) were detected in trophoblast cells treated with sera obtained from preeclamptic patients, but not in trophoblast cells treated with sera from normotensive controls. However, all the groups express the pro-form (p30) of caspase-3. This suggests that the apoptotic cascade is activated only in trophoblast cells treated with pre-disease serum.

Caspase-3 Assay

Caspase-3 substrate (Ac-DEVD-pNA) was added to a final concentration of 200 µM in 100 µl reactions containing 100 mM HEPES (pH 7.5), 10% sucrose, 0.1% CHAPS, 2% DMSO, and 10 mM DTT in a 96 well plate. Plates were incubated at 37° C. for 4 hours. Absorbance of the cleaved product was read at 405 nm using Dynatech MR5000 plate reader. Blank values were subtracted and relative activity was calculated based on activity from untreated cells.

REFERENCES

1. ROBERTS J M. Preeclampsia: what we know and what we do not know. Semin Perinatol 2000;24:24-8.
2. ANONYMOUS. Do women with preeclampsia, and their babies, benefit from magnesium sulphate? The Magpie Trial: a randomised placebo-controlled trial. Lancet 2002;359:1877-90.
3. BROSENS I, DIXON H G, ROBERTSON W B. Fetal growth retardation and the arteries of the placental bed. Br J Obstet Gynaecol 1977;84:656-63.
4. PIJNENBORG R. Establishment of uteroplacental circulation. Reprod Nutr Dev 1988;28:1581-1586.
5. KIM Y M, CHAIWORAPONGSA T, GOMEZ R, et al. Failure of physiologic transformation of the spiral arteries in the placental bed in preterm premature rupture of membranes. Am J Obstet Gynecol 2002;187:1137-42.
6. ROBERTSON W B, BROSENS I, DIXON G. Maternal uterine vascular lesions in the hypertensive complications of pregnancy. Perspect Nephrol Hypertens 1976;5:115-27.
7. KHONG T Y, DE WOLF F, ROBERTSON W B, BROSENS I. Inadequate maternal vascular response to placentation in pregnancies complicated by preeclampsia and by small-for-gestational age infants. Br J Obstet Gynaecol 1986; 93:1049-59.
8. ZHOU Y, DAMSKY C H, FISHER S J. Preeclampsia is associated with failure of human cytotrophoblasts to mimic a vascular adhesion phenotype. One cause of defective endovascular invasion in this syndrome? J Clin Invest 1997;99:2152-64.
9. FISHER S J. The placenta dilemma. Semin Reprod Med 2000;18:321-6.
10. DE WOLF F, DE WOLF-PEETERS C, BROSENS I. Ultrastructure of the spiral arteries in the human placental bed at the end of normal pregnancy. Am J Obstet Gynecol 1973;117:833-48.
11. DE WOLF F, ROBERTSON W B, BROSENS I. The ultrastructure of acute atherosis in hypertensive pregnancy. Am J Obstet Gynecol 1975;123:164-74.
12. BUEMI M, ALLEGRA A, D'ANNA R, et al. Is apoptosis cause of preeclampsia? Eur Rev Med Pharmacol Sci 1998;2:185-8.
13. LEVY R, NELSON D M. To be, or not to be, that is the question. Apoptosis in human trophoblast. Placenta 2000;21:1-13.
14. MOR G, STRASZEWSKI S, KAMSTEEG M. Role of the Fas/Fas ligand system in female reproductive organs: survival and apoptosis. Biochem Pharmacol 2002;64:1305.
15. STRASZEWSKI S L, ABRAHAMS V M, FUNAI E, MOR G. Xiap Confers Human Trophoblast Cell Resistance to Fas-Mediated Apoptosis. Molecular Human Reproduction 2004; in press.
16. SMITH S C, BAKER P N, SYMONDS E M. Increased placental apoptosis in intrauterine growth restriction. Am J Obstet Gynecol 1997;177:1395-401.
17. LEVY R, SMITH S D, YUSUF K, et al. Trophoblast apoptosis from pregnancies complicated by fetal growth restriction is associated with enhanced p53 expression. Am J Obstet Gynecol 2002;186:1056-61.
18. SMITH S C, BAKER P N, SYMONDS E M. Placental apoptosis in normal human pregnancy. Am J Obstet Gynecol 1997;177:57-65.
19. ASCHKENAZI S, STRASZEWSKI S, VERWER K M, FOELLMER H, RUTHERFORD T, MOR G. Differential regulation and function of the fas/fas ligand system in human trophoblast cells. Biol Reprod 2002;66:1853-61.
20. NEALE D, DEMASIO K, ILLUZI J, CHAIWORAPONGSA T, ROMERO R, MOR G. Maternal serum of women with preeclampsia reduces trophoblast cell viability: evidence for an increased sensitivity to Fas-mediated apoptosis. J Matern Fetal Neonatal Med 2003;13:39-44.
21. GYNECOLOGISTS ACoOA. The Compendium. In: ACOG, ed. Hypertension and pregnancy. Washington D.C., 2000 (vol Technical Bulletin 219).
22. SONG J, RUTHERFORD T, BROWN S, MOR G. Hormonal regulation of Fas and FasL expression and apoptosis in the normal human endometrium. Molecular Human Reproduction 2002;8:447-455.
23. SONG J, SAPI E, BROWN W, et al. Roles of Fas and Fas ligand during mammary gland remodeling. J Clin Invest 2000;106:1209-20.
24. ABRAHAMS V, STRASZEWSKI S, KAMSTEEG M, et al. Epithelial Ovarian Cancer secrete funcitonal Fas Ligand. Cancer Res 2003;63:5573-5581.
25. WILLIAMS J. Premature separation of the normally implanted placenta. Surg Gynecol Obstet 1915;21:541-554.
26. CHESLEY L C. The control of hypertension in pregnancy. Obstet Gynecol Annu 1981;10:69-106.
27. TATUM H J, MULE J G. The hypertensive action of blood from patients with preeclampsia. Am J Obstet Gynecol 1962;83:1028-35.
28. TATUM H J. The Obstetric Patient with Toxemia. Clin Obstet Gynecol 1964;13:233-48.
29. PIRANI B B, MACGILLIVRAY I. The effect of plasma retransfusion on the blood pressure in the puerperium. Am J Obstet Gynecol 1975;121:221-6.
30. GANT N F, CHAND S, WHALLEY P J, MACDONALD P C. The nature of pressor responsiveness to angiotensin II in human pregnancy. Obstet Gynecol 1974;43:854.

31. Gant N F, Daley G L, Chand S, Whalley P J, MacDonald P C. A study of angiotensin II pressor response throughout primigravid pregnancy. J Clin Invest 1973; 52:2682-9.
32. Zuspan F P. Catecholamines. Their role in pregnancy and the development of pregnancy-induced hypertension. J Reprod Med 1979;23:143-50.
33. Zuspan F P. Urinary amine alterations in drug-addiction pregnancy. Am J Obstet Gynecol 1976;126:955-64.
34. Krege J H, Katz V L. A proposed relationship between vasopressinase altered vasopressin and preeclampsia. Med Hypotheses 1990;31:283-7.
35. Mckinney E T, Shouri R, Hunt R S, Ahokas R A, Sibai B M. Plasma, urinary, and salivary 8-epi-prostaglandin f2alpha levels in normotensive and preeclamptic pregnancies. Am J Obstet Gynecol 2000;183:874-7.
36. Clark B A, Halvorson L, Sachs B, Epstein F H. Plasma endothelin levels in preeclampsia: elevation and correlation with uric acid levels and renal impairment. Am J Obstet Gynecol 1992;166:962-8.
37. Pedersen E B, Aalkjaer C, Christensen N J, et al. Renin, angiotensin II, aldosterone, catecholamines, prostaglandins and vasopressin. The importance of pressor and depressor factors for hypertension in pregnancy. Scand J Clin Lab Invest Suppl 1984;169:48-56.
38. Aalkjaer C, Johannesen P, Pedersen E B, Rasmussen A, Mulvany M J. Morphology and angiotensin II responsiveness of isolated resistance vessels from patients with preeclampsia. Scand J Clin Lab Invest Suppl 1984;169: 57-60.
39. Chua S, Wilkins T, Sargent I, Redman C. Trophoblast deportation in pre-eclamptic pregnancy. Br J Obstet Gynaecol 1991;98:973-9.
40. Johansen M, Redman C W, Wilkins T, Sargent I L. Trophoblast deportation in human pregnancy—its relevance for preeclampsia. Placenta 1999;20:531-9.
41. Sargent I L, Johansen M, Chua S, Redman C W. Clinical experience: isolating trophoblasts from maternal blood. Ann N Y Acad Sci 1994;731:154-61.
42. Knight M, Redman C W, Linton E A, Sargent I L. Shedding of syncytiotrophoblast microvilli into the maternal circulation in pre-eclamptic pregnancies. Br J Obstet Gynaecol 1998;105:632-40.
43. Kertesz Z, Hurst G, Ward M, et al. Purification and characterization of a complex from placental syncytiotrophoblast microvillous membranes which inhibits the proliferation of human umbilical vein endothelial cells. Placenta 1999;20:71-9.
44. Yoon B H, Romero R, Jun J K, et al. Amniotic fluid cytokines (interleukin-6, tumor necrosis factor-alpha, interleukin-1 beta, and interleukin-8) and the risk for the development of bronchopulmonary dysplasia. Am J Obstet Gynecol 1997;177:825-30.
45. Genbacev O, Difederico E, Mcmaster M, Fisher S J. Invasive cytotrophoblast apoptosis in preeclampsia. Hum Reprod 1999;14 Suppl 2:59-66.
46. Miller M J, Voelker C A, Olister S, et al. Fetal growth retardation in rats may result from apoptosis: role of peroxynitrite. Free Radic Biol Med 1996;21:619-29.
47. Loke Y W, Butterworth B H, Margetts J J, Burland K. Identification of cytotrophoblast colonies in cultures of human placental cells using monoclonal antibodies. Placenta 1986;7:221-31.
48. Roberts J M, Redman C W. Preeclampsia: more than pregnancy-induced hypertension. Lancet 1993;341:1447-51.
49. Ashkenazi A, Dixit V M. Death receptors: signaling and modulation. Science 1998;281:1305-8.
50. Nagata S. Fas and Fas ligand: a death factor and its receptor. Adv. Immunol 1994;57:129-135.
51. Nagata S. Apoptosis by death factor. Cell 1997;88:355-365.
52. Mor G, Gutierrez L, Eliza M, Kahyaoglu F, Arici A. Fas-Fas ligand system induced apoptosis in human placenta and gestational trophoblastic disease. American Journal of Reproductive Immunology 1998;40:89-95.
53. Berridge M V, Tan A S. Characterization of the cellular reduction of 3-(4,5-dimethylthiazol-2-yl)-2,5-diphenyltetrazolium bromide (MTT): subcellular localization, substrate dependence, and involvement of mitochondrial electron transport in MTT reduction. Arch Biochem Biophys 1993;303:474-82.
54. Athayde N, Romero R, Maymon E, et al. Interleukin 16 in pregnancy, parturition, rupture of fetal membranes, and microbial invasion of the amniotic cavity. Am J Obstet Gynecol 2000;182:135-41.
55. Romero R, Maymon E, Pacora P, et al. Further observations on the fetal inflammatory response syndrome: a potential homeostatic role for the soluble receptors of tumor necrosis factor alpha. Am J Obstet Gynecol 2000; 183:1070-7.
56. Rudin C M, Thompson C B. Apoptosis and disease: regulation and clinical relevance of programmed cell death. Annu Rev Med 1997;48:267-81.
57. Difederico E, Genbacev O, Fisher S J. Preeclampsia is associated with widespread apoptosis of placental cytotrophoblasts within the uterine wall. Am J Pathol 1999;155:293-301.
58. Jarvis J N, Deng L, Berry S M, Romero R, Moore H. Fetal cytokine expression in utero detected by reverse transcriptase polymerase chain reaction. Pediatr Res 1995;37:450-4.
59. Rinehart B K, Terrone D A, Lagoo-Deenadayalan S, et al. Expression of the placental cytokines tumor necrosis factor alpha, interleukin 1beta, and interleukin 10 is increased in preeclampsia. Am J Obstet Gynecol 1999; 181:915-20.
60. Clark P, Boswell F, Greer I A. The neutrophil and preeclampsia. Semin Reprod Endocrinol 1998; 16:57-64.
61. Greer I A, Dawes J, Johnston T A, Calder A A. Neutrophil activation is confined to the maternal circulation in pregnancy-induced hypertension. Obstet Gynecol 1991; 78:28-32.
62. Greer I A, Haddad N G, Dawes J, Johnstone F D, Calder A A. Neutrophil activation in pregnancy-induced hypertension. Br J Obstet Gynaecol 1989;96:978-82.
63. Gervasi M T, Chaiworapongsa T, Naccasha N, et al. Phenotypic and metabolic characteristics of maternal monocytes and granulocytes in preterm labor with intact membranes. Am J Obstet Gynecol 2001; 185:1124-9.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for determining if a pregnant woman is at risk of developing preeclampsia, comprising:
   (a) culturing human trophoblast cells in the presence of (i) anti-Fas antibodies and (ii) serum or plasma obtained from a pregnant woman to be assessed for risk of developing preeclampsia, wherein the serum or plasma is from the first trimester of pregnancy;
   (b) culturing an equivalent sample of human trophoblast cells under the same conditions as cells in (a) but in the absence of serum or plasma obtained from a pregnant woman to be assessed for risk of developing preeclampsia; and
   (c) comparing viability of cells cultured in (a) with the viability of cells cultured in (b), wherein if fewer cells cultured in (a) than cells cultured in (b) are viable, the woman is determined to be at risk of developing preeclampsia.

2. A method for determining if a pregnant woman is at risk of developing preeclampsia, comprising:
   (a) culturing human trophoblast cells in the presence of anti-Fas antibodies;
   (b) culturing cells from (a) in the presence of serum or plasma obtained from a pregnant woman to be assessed for risk of developing preeclampsia, wherein the serum or plasma is from as early as the first trimester of pregnancy;
   (c) culturing an equivalent sample of cells from (a) under the same conditions as cells in (b) but in the absence of serum or plasma obtained from a pregnant woman to be assessed for risk of developing preeclampsia; and
   (d) comparing viability of cells cultured in (b) with the viability of cells cultured in (c), wherein if fewer cells cultured in (b) than cells cultured in (c) are viable, the woman is determined to be at risk of developing preeclampsia.

3. The method of claim 1, further comprising:
   (d) culturing an equivalent sample of human trophoblast cells under the same conditions as cells in (a) but in the presence of serum or plasma obtained from a normal control; and
   (e) comparing viability of cells cultured in (a) with the viability of cells cultured in (d), wherein if fewer cells cultured in (a) than cells cultured in (d) are viable, the woman is at risk of developing preeclampsia.

4. The method of claim 2, further comprising:
   (e) culturing an equivalent sample of cells from (a) under the same conditions as cells in (b) but in the presence of serum or plasma obtained from a normal control; and
   (f) comparing viability of cells cultured in (b) with the viability of cells cultured in (e), wherein if fewer cells cultured in (b) than cells cultured in (e) are viable, the woman is at risk of developing preeclampsia.

5. The method of claim 1, wherein the pregnant woman is in the first trimester of pregnancy.

6. The method of claim 2, wherein the pregnant woman is in the first trimester of pregnancy.

7. The method of claim 2, wherein the pregnant woman is in the third trimester of pregnancy.

* * * * *